United States Patent [19]

Nappa et al.

[11] Patent Number: 5,414,165
[45] Date of Patent: May 9, 1995

[54] PROCESS FOR THE MANUFACTURE OF 1,1,1,3,3,3,-HEXAFLUOROPROPANE

[75] Inventors: Mario J. Nappa, Newark, Del.; Allen C. Sievert, Elkton, Md.

[73] Assignee: E. I. Du Pont de Nemours and Company, Wilmington, Del.

[21] Appl. No.: 282,940

[22] Filed: Jul. 29, 1994

[51] Int. Cl.$^6$ ............................................. C07C 17/08
[52] U.S. Cl. ....................................... 570/169; 570/168
[58] Field of Search ......................... 570/169, 166, 168

[56] References Cited

U.S. PATENT DOCUMENTS

| | | | |
|---|---|---|---|
| 3,859,424 | 1/1975 | Scherer et al. | 423/472 |
| 4,843,181 | 6/1989 | Gumprecht et al. | 570/169 |
| 5,036,036 | 7/1991 | Lerou | 502/317 |
| 5,171,901 | 12/1992 | Gassen et al. | 570/168 |
| 5,177,273 | 1/1993 | Bruhnke | 570/166 |
| 5,347,059 | 9/1994 | Pennetreau | 570/166 |

FOREIGN PATENT DOCUMENTS 2073533  1/1993  Canada ..................... C07C 19/08

*Primary Examiner*—Alan Siegel

[57] ABSTRACT

A process is disclosed for producing 1,1,1,3,3,3-hexafluoropropane with high selectivity. 1,1,1,3,3,3-hexachloropropane is contacted with hydrogen fluoride in the vapor phase at a temperature of from about 200° C. to 400° C. in the presence of a catalyst comprising trivalent chromium, to produce a fluorinated product containing $CF_3CH_2CF_3$ and its haloprecursors (i.e., compounds which may be recycled for further reaction with HF) with a total selectivity of at least about 95 percent; and a sufficient amount of said haloprecursors is reacted with hydrogen fluoride in the vapor phase at a temperature of from 200° C. to 400° C. in the presence of a catalyst comprising trivalent chromium to provide an overall selectivity to 1,1,1,3,3,3-hexafluoropropane of at least about 95 percent based upon the amount of 1,1,1,3,3,3-hexachloropropane initially reacted with HF.

6 Claims, No Drawings

PROCESS FOR THE MANUFACTURE OF 1,1,1,3,3,3,-HEXAFLUOROPROPANE

FIELD OF THE INVENTION

This invention relates to a process for the manufacture of 1,1,1,3,3,3-hexafluoropropane (i.e., $CF_3CH_2CF_3$ or HFC-236fa) by the reaction of 1,1,1,3,3,3-hexachloropropane (i.e., $CCl_3CH_2CCl_3$ or HCC-230fa) with hydrogen fluoride.

BACKGROUND

HFC-236fa is useful as a refrigerant, fire extinguishant, heat transfer medium, gaseous dielectric, sterilant carrier, polymerization medium, particulant removal fluid, carrier fluid, buffing abrasive agent, displacement drying agent and power cycle working fluid. More particularly, HFC-236fa is a highly effective and environmentally acceptable refrigerant.

Canadian Patent No. 2,073,533 discloses a liquid phase process for the manufacture of HFC-236fa by contacting HCC-230fa with HF in the presence of a liquid phase catalyst (e.g., tin and antimony compounds). All of the 1,1,1,3,3,3-hexachloropropane is converted to 1-chloro-1,1,3,3,3-pentafluoropropane (i.e., HCFC-235fa) and HFC-236fa with a selectivity of greater than 45 mole with respect to HFC-236fa. The separation of pure HFC-236fa is complicated by the presence of HCFC-235fa. Moreover, vapor processes are often preferred because operational advantages (e.g., HF corrosivity problems are typically exacerbated in the liquid phase).

HFC-236fa has been prepared by vapor phase chlorine substitution processes in which the yields have typically been less than about 70%. For example, U.S. Pat. No. 5,171,901 discloses a process for the preparation of HFC-236fa by contacting a mixture of hexachloropropene and HF with a catalyst consisting of a mixture of $CrCl_3$ and $MgF_2$ at temperatures ranging from 350° C. to 500° C. The reaction temperatures and yields of HFC-236fa were as follows: 350° C., none detected; 400° C., 10%; 450° C., 55%; and 500° C., 64%. Other products formed in varying amounts were $CF_3CHClCF_3$, $CF_3CCl_2CF_3$, $CF_3CCl=CF_2$, $CF_3CCl=CClF$, and $CF_3CCl=CCl_2$.

U.S. Pat. No. 3,859,424 discloses (Example 10) a process for the reaction of 1,1,1,3-tetrachloropropane and HF over a fluorinated chromium oxide catalyst at 200° C. The major product (58%) obtained was 1,1,1-trifluoropropene; the other product (28.5%) was 1,1,1-trifluoro-3-chloropropane.

There is an interest in developing more efficient vapor phase processes for the manufacture of HFC-236fa.

SUMMARY OF THE INVENTION

A process is provided in accordance with this invention for producing 1,1,1,3,3,3-hexafluoropropane which comprises (1) contacting 1,1,1,3,3,3-hexachloropropane with hydrogen fluoride in the vapor phase at a temperature of from about 200° C. to 400° C. in the presence of a catalyst comprising trivalent chromium, to produce a fluorinated product containing $CF_3CH_2CF_3$ and its haloprecursors with a total selectivity of at least about 95 percent; and (2) reacting a sufficient amount of said haloprecursors with hydrogen fluoride in the vapor phase at a temperature of from 200° C. to 400° C. in the presence of a catalyst comprising trivalent chromium to provide an overall selectivity to 1,1,1,3,3,3-hexafluoropropane of at least about 95 percent based upon the amount of 1,1,1,3,3,3-hexachloropropane reacted with HF in (1).

DETAILED DESCRIPTION

The present invention provides a process for the manufacture of 1,1,1,3,3,3-hexafluoropropane (i.e., $CF_3CH_2CF_3$ or HFC-236fa) by contacting a mixture of hydrogen fluoride and 1,1,1,3,3,3-hexachloropropane (i.e., $CCl_3CH_2CCl_3$ or HCC-230fa) in the vapor phase in the presence of a trivalent chromium catalyst. The trivalent chromium catalyst may be unsupported (e.g., $Cr_2O_3$) or supported (e.g., on alumina, aluminum fluoride, magnesium fluoride or carbon). The starting material, HCC-230fa, can be prepared by the reaction of carbon tetrachloride with vinylidene chloride as disclosed in Belbachir et al. Makromol. Chem., Vol. 185, pp. 1583–1595 (1984) (see Chemical Abstracts 101:131167).

The catalysts of the present invention are used to provide highly selective production of HFC-236fa and its haloprecursors. By haloprecursors of $CF_3CH_2CF_3$ is meant saturated compounds of the formula $CX_3CH_2CX_2Cl$ and olefinic compounds of the formula $CX_2=CHCX_3$ where each X is Cl or F and at least one X in the haloprecursor compound is F. These haloprecursors may be recycled to the reaction for further reaction with HF in the presence of trivalent chromium to produce additional HFC-236fa such that the overall selectivity to 236fa from 230fa is high. Of note are embodiments where the process is run to produce HFC-236fa itself with a selectivity of at least about 95 percent prior to separation of the HFC-236fa from the haloprecursors or other reaction by-products. This may be achieved for example by providing sufficient catalyst contact time in a single pass reaction system to allow substantially complete replacement of chlorine by fluorine and saturation of any olefinic haloprecursors. Alternatively, the reactor effluent can be cycled (optionally with additional HF) for further catalyst contact.

Preferred catalysts (especially where selectivity to HFC-236fa of about 95 percent or more is desired prior to separation of the HFC-236fa from the haloprecursors or other reaction by-products) include $Cr_2O_3$ prepared by pyrolysis of $(NH_4)_2Cr_2O_7$, $Cr_2O_3$ having a surface area greater than about 200 m$^2$/g, and $Cr_2O_3$ prepared by pyrolysis of $(NH_4)_2Cr_2O_7$ or having a surface area greater than about 200 m$^2$/g which is pretreated with a vaporizable fluorine-containing compound (e.g., HF or $CCl_3F$). These pretreated catalysts are most preferred, and are suitable for obtaining at least about 99% selectivity to HFC-236 itself prior to separation of the HFC-236fa from its haloprecursors or other reaction by-products (e.g., in a single pass over the catalyst).

The $Cr_2O_3$ catalyst prepared by the pyrolysis of ammonium dichromate suitable for the process of this invention can be prepared by any method known to the art including those disclosed in U.S. Pat. Nos. 4,843,181 and 5,036,036, which are hereby incorporated herein by reference. The $Cr_2O_3$ obtained by such pyrolysis may contain low levels of contaminants which are present as a result of the manufacturing process for the original $(NH_4)_2Cr_2O_7$. Although not totally destructive of catalyst efficacy, potassium, for example, as a contaminant has an adverse effect on the activity and life of the catalyst of this invention. It is desirable for the amount of potassium and other alkali metals to be 100 ppm by weight or less. The level may be reduced by a water-washing step. While the conditions are not critical, the water-washing step can include forming a slurry containing 5–15% $Cr_2O_3$, preferably 10%, and deionized water. Stirring of this water slurry can be carried out at 35°–65° C. for at least one hour, preferably two or more hours. The solids are then recovered by filtration, suitably on a plate and frame filter press. The filter cake can be analyzed for alkali metal content. If its level is 100 ppm by weight or less (dry basis), the solids are, thereafter, dried. If not, the washing step can be repeated to obtain a desired level of alkali metal content.

Other $Cr_2O_3$ catalysts which may be used in the process of this invention include catalysts having a surface area greater than about 200 $m^2/g$, some of which are commercially available.

The form of the catalyst is not critical and may be used as pellets, powders or granules.

Generally, the resulting $Cr_2O_3$ will be pretreated with HF. It is thought that this converts some of the surface chrome oxide to chrome oxyfluoride. This pretreatment can be accomplished by placing the $Cr_2O_3$ in a suitable container, which can be the reactor to be used to perform the reaction of the instant invention, and thereafter, passing HF over the pyrolyzed and dried $Cr_2O_3$ so as to partially saturate the $Cr_2O_3$ with HF. This is conveniently carried out by passing HF over the $Cr_2O_3$ for a period of time, for example, about 15 to 300 minutes at a temperature of, for example, about 200° C. to about 450° C. The purpose of this pretreatment is to prevent damage to the catalyst due to possible high temperature excursions and resultant coking of the catalyst if the organic reactants were contacted with the catalyst without first having conditioned some of the surface chrome oxide with HF. Nevertheless, this pretreatment is not essential; initial process conditions and equipment could be selected so as to avoid the problem of high temperature and coking of the catalyst.

The molar ratio of HF to $CCl_3CH_2CCl_3$ typically ranges from about 1:1 to about 100:1, and is preferably within the range of about 6:1 to about 20:1. HF:$CCl_3CH_2CCl_3$ ratios lower than about 6 result in incomplete conversion of the 1,1,1,3,3,3-hexachloropropane starting material. HF:$CCl_3CH_2CCl_3$ ratios greater than about 20 have little advantage and result in large amounts of HF being recycled or discarded.

The process of the present invention is suitably conducted at a temperature in the range of from about 200° C. to 400° C., preferably from about 225° C. to about 350° C., and more preferably, from about 250° C. to 325° C. Temperatures below about 200° C. result in low conversion of the 1,1,1,3,3,3-hexachloropropane starting material. The contact time of reactants with the catalyst bed is typically from about 0.2 second to about 60 seconds.

The pressure is not critical but should be sufficient to maintain HF, 1,1,1,3,3,3-hexachloropropane and the reaction product stream components in the vapor state at the operating temperature.

In general, the higher the temperature, the greater the HF reactant mole ratio, and the longer the contact time, the greater is the conversion of 1,1,1,3,3,3-hexachloropropane to HFC-236fa.

The reaction products may be separated by conventional techniques such as distillation. 1,1,1,3,3,3-Hexafluoropropane and HF form an azeotrope which can be recovered from the reaction products by using conventional techniques such as decantation and distillation. Reaction products such as $CF_3CH=CCl_2$, $CCl_2FCH=CF_2$, or $CF_3CH_2CClF_2$ which are haloprecursors of HFC-236fa can be separated from the reaction products and advantageously returned to the reactor for conversion to $CF_3CH_2CF_3$.

The process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel ® nickel-copper alloys, Hastelloy ® nickel-based alloys and, Inconel ® nickel-chromium alloys, and copper-clad steel. Silicon carbide is also suitable for reactor fabrication.

Practice of the invention will become further apparent from the following non-limiting examples.

EXAMPLES

EXAMPLE 1

$CCl_3CH_2CCl_3 + HF \rightarrow CF_3CH_2CF_3$

A 15 in. (38.1 cm)×⅜ in. (0.95 cm) Hastelloy ™ nickel alloy tube was filled with $Cr_2O_3$, prepared by the pyrolysis of ammonium dichromate, (17.1 g, 15 mL, 12 to 20 mesh (1.4 to 0.83 mm)). The $Cr_2O_3$ was activated by heating at 250° C. for 65.3 hours under a nitrogen purge (20 sccm, $3.3 \times 10^{-7}$ $m^3/s$). The temperature was raised to 300° C., the nitrogen was turned off and the reactor purged with HF (20 sccm, $3.3 \times 10^{-7}$ $m^3/s$) for 95 minutes. The temperature was raised to 450° C. and the HF flow was raised to 200 sccm ($3.3 \times 10^{-6}$ $m^3/s$) for 75 minutes. The temperature was then lowered to 250° C. and the HF flow reduced to 24 sccm ($4.0 \times 10^{-7}$ $m^3/s$) for 15 minutes.

The reactor temperature was raised to 300° C. and $CCl_3CH_2CCl_3$ was fed to the reactor at a flow rate of 1.12 mL/h (3.0 sccm, $5.0 \times 10^{-8}$ $m^3/s$), along with HF at a flow rate of 36 sccm ($6.0 \times 10^{-7}$ $m^3/s$) and nitrogen at a flow rate of 2 sccm ($3.3 \times 10^{-8}$ $m^3/s$). The gaseous effluent was analyzed by GC/MS and found to be 99% $CF_3CH_2CF_3$, 0.7% of an isomer of $C_3HCl_2F_3$, and 0.4% of an unknown.

EXAMPLE 2

A 15 in. (38.1 cm)×⅜ in. (0.95 cm) Hastelloy ™ nickel alloy tube was filled with 5.17 grams (5 mL) of a high surface area (>200 $m^2/gm$) Calsicat ® chrome oxide ground to 12–20 mesh (1.4 to 0.83 mm). The catalyst was activated by first drying at 200° C. for 2.5 hours under a nitrogen purge (100 sccm, $1.7 \times 10^{-7}$ $m^3/s$). The nitrogen was reduced to 50 sccm ($8.3 \times 10^{-7}$ $m^3/s$) and the catalyst contacted with HF (50 sccm, $8.3 \times 10^{-7}$ $m^3/s$) for 40 minutes. The HF flow was raised to 80 sccm ($1.3 \times 10^{-6}$ $m^3/s$) and the nitrogen flow reduced to 20 sccm ($3.3 \times 10^{-7}$ $m^3/s$) for 35 minutes. The temperature was raised to 400° C. for 25 minutes and then reduced back down to 250° C. for 30 minutes.

At 250° C., a $CCl_3CH_2CCl_3$ flow of 0.43 mL/hr (1.2 sccm, $2.0 \times 10^{-8}$ $m^3/s$) and HF flow of 14 sccm ($2.3 \times 10^{-7}$ $m^3/s$) were fed through the reactor. The gaseous effluent was analyzed by GC-MS and found to be 99% $CF_3CH_2CF_3$, 0.8% $CF_3CHCl$ $CF_3$, and 0.2% of a $C_3HCl_2F_3$ isomer.

EXAMPLE 3

A 15 in. (38.1 cm)×⅜ in. (0.95 cm) Hastelloy ™ nickel alloy tube was filled with 1.96 grams (5 mL) of $CrCl_3$/carbon (29% $CrCl_3$ by weight). The catalyst was activated by heating it to 200° C. for 75 minutes while purging with nitrogen (100 sccm, $1.7 \times 10^{-6}$ m$^3$/s). The nitrogen flow was reduced to 50 sccm ($8.3 \times 10^{-7}$ m$^3$/s) and the HF flow begun at 50 sccm ($8.3 \times 10^{-7}$ m$^3$/s) for 45 minutes. The HF was then raised to 80 sccm ($1.3 \times 10^{-6}$ m$^3$/s) and the nitrogen flow reduced to 20 sccm ($3.3 \times 10^{-7}$ m$^3$/s) for 25 minutes. The temperature of the reactor was raised to 250° C. for 50 minutes, raised to 300° C. for 55 minutes, raised to 350° C. for 45 minutes, raised to 400° C. for 60 minutes, and then cooled to 200° C. for 95 minutes.

At 250° C., a $CCl_3CH_2CCl_3$ flow of 0.43 mL/hr (1.2 sccm, $2.0 \times 10^{-8}$ m$^3$/s) and HF flow of 14 sccm ($2.3 \times ^{-7}$ m$^3$/s) were fed through the reactor. The major product contained primarily $C_3HCl_2F_3$ along with about 2% $CF_3CH_2CF_3$. Increasing the temperature to 300° C. resulted in a product mixture containing 95% $C_3HCl_2F_3$ isomer and 4.4% $CF_3CH_2CF_3$. The unsaturated product, $C_3HCl_2F_3$, is considered suitable for recycle to produce additional $CF_3CH_2CF_3$.

What is claimed is:

1. A process for producing 1,1,1,3,3,3-hexafluoropropane, comprising:
   (1) contacting 1,1,1,3,3,3-hexachloropropane with hydrogen fluoride in the vapor phase at a temperature of from about 200° C. to 400° C. in the presence of a catalyst comprising trivalent chromium, to produce a fluorinated product containing $CF_3CH_2CF_3$ and its haloprecursors with a total selectivity of at least about 95 percent; and
   (2) reacting a sufficient amount of said haloprecursor with hydrogen fluoride in the vapor phase at a temperature of from about 200° C. to 400° C. in the presence of a catalyst comprising trivalent chromium, to provide an overall selectivity to 1,1,1,3,3,3-hexafluoropropane of at least about 95 percent based upon the amount of 1,1,1,3,3,3-hexachloropropane reacted with HF in (1).

2. The process of claim 1 wherein the catalyst of (1) and (2) is selected from the group consisting of catalysts prepared by pyrolysis of $(NH_4)_2Cr_2O_7$ to produce $Cr_2O_3$ and pretreatment with HF and catalysts prepared by pretreating $Cr_2O_3$ having a surface area greater than about 200 m$^2$/g with HF.

3. The process of claim 2 wherein 1,1,1,3,3,3-hexafluoropropane itself is produced with a selectivity of at least about 99 percent prior to separation of the 1,1,1,3,3,3-hexafluoropropane from said haloprecursors or other reaction by-products.

4. The process of claim 1 wherein the temperature of (1) and (2) is from about 225° C. to 350° C.

5. The process of claim 1 wherein the temperature of (1) and (2) is from about 250° C. to 325° C.

6. The process of claim 1 wherein the mole ratio of HF to 1,1,1,3,3,3-hexachloropropane is within the range of about 6:1 to 20:1.

* * * * *